(12) United States Patent
Abele et al.

(10) Patent No.: US 8,547,633 B2
(45) Date of Patent: Oct. 1, 2013

(54) OPERATING MICROSCOPE AND METHOD FOR PIVOTING A CO-OBSERVER MICROSCOPE

(75) Inventors: Alfons Abele, Schwaebisch Gmuend (DE); Rupert Demleitner, Heidenheim (DE); Daniel Kolster, Oberkochen (DE)

(73) Assignee: Carl Zeiss Surgical GmbH (DE)

( * ) Notice: Subject to any disclaimer, the term of this patent is extended or adjusted under 35 U.S.C. 154(b) by 322 days.

(21) Appl. No.: 12/851,183

(22) Filed: Aug. 5, 2010

(65) Prior Publication Data

US 2011/0032607 A1    Feb. 10, 2011

(30) Foreign Application Priority Data

Aug. 7, 2009  (DE) .......................... 10 2009 037 022

(51) Int. Cl.
*G02B 21/00*    (2006.01)

(52) U.S. Cl.
USPC .......................................... 359/384; 359/376

(58) Field of Classification Search
USPC .......................................... 359/375, 376, 384
See application file for complete search history.

(56) References Cited

U.S. PATENT DOCUMENTS

| | | | | |
|---|---|---|---|---|
| 4,341,435 A * | 7/1982 | Lang et al. | ..................... | 359/376 |
| 4,605,287 A | 8/1986 | Lang et al. | | |
| 5,689,365 A * | 11/1997 | Takahashi | ..................... | 359/362 |
| 5,898,518 A | 4/1999 | Biber | | |
| 6,172,804 B1 * | 1/2001 | Schuck et al. | ................ | 359/384 |
| 6,333,813 B1 * | 12/2001 | Morita et al. | ................. | 359/368 |
| 6,421,173 B1 * | 7/2002 | Corbisiero et al. | ........... | 359/372 |
| 6,614,595 B2 * | 9/2003 | Igarashi | ........................ | 359/464 |
| 7,265,899 B2 * | 9/2007 | Morita | ........................... | 359/384 |
| 7,633,676 B2 * | 12/2009 | Brunner et al. | ................ | 359/369 |
| 8,154,795 B2 * | 4/2012 | Schnitzler et al. | ............. | 359/384 |
| 8,284,482 B2 * | 10/2012 | Strahle et al. | ................. | 359/368 |
| 2004/0017607 A1 * | 1/2004 | Hauger et al. | ................. | 359/376 |
| 2004/0105147 A1 | 6/2004 | Hermann et al. | | |
| 2006/0023300 A1 | 2/2006 | Sander | | |
| 2008/0239473 A1 | 10/2008 | Takagi | | |
| 2011/0170179 A1 * | 7/2011 | Strahle et al. | ................. | 359/376 |

FOREIGN PATENT DOCUMENTS

| | | |
|---|---|---|
| DE | 1 217 099 | 5/1966 |
| DE | 197 18 102 | 12/1997 |
| DE | 10 2004 049 368 | 4/2006 |
| DE | 10 2008 024 732 | 1/2010 |
| EP | 1 089 107 | 9/2000 |

* cited by examiner

*Primary Examiner* — Frank Font
(74) *Attorney, Agent, or Firm* — Gerald E. Hespos; Michael J. Porco; Matthew T. Hespos

(57) ABSTRACT

An operating microscope has a main objective (1) that extends along an objective plane and is penetrated by a binocular main observer beam path and a binocular co-observer beam path. The binocular main observer beam path has two main observation pupils (3a, 3b) in the objective plane with centers on a first straight line (7). The binocular co-observer beam path has two co-observation pupils (5a, 5b) in the objective plane with centers on a second straight line (9). The first and second straight lines (7, 9) intersect. The co-observer beam path can be displaced with respect to the main observer beam path so that the angle between the second and first straight line (9, 7) changes. The center point (6) between the co-observation pupils (5a, 5b) in the objective plane displaces when there is a change in the angle between the second and first imagined straight lines (9, 7).

17 Claims, 3 Drawing Sheets

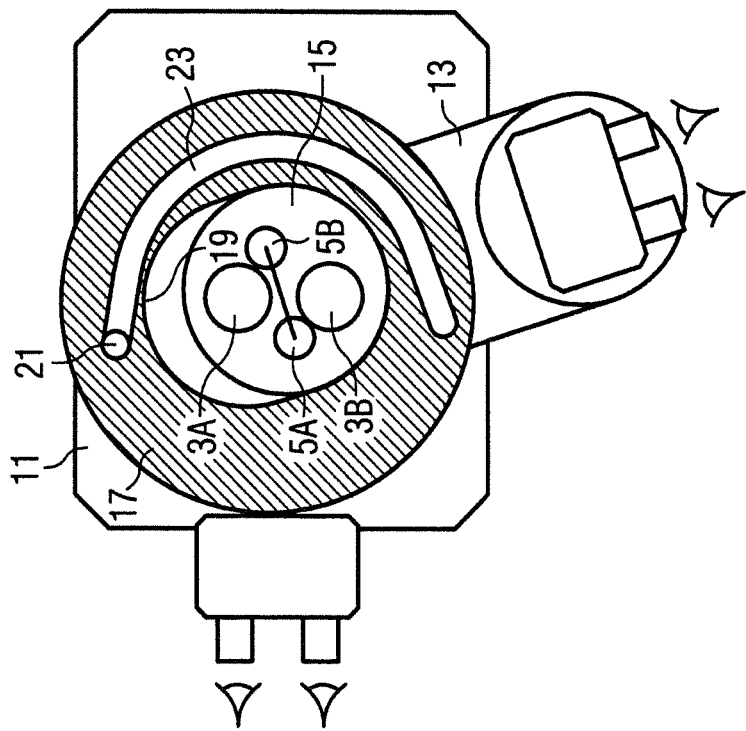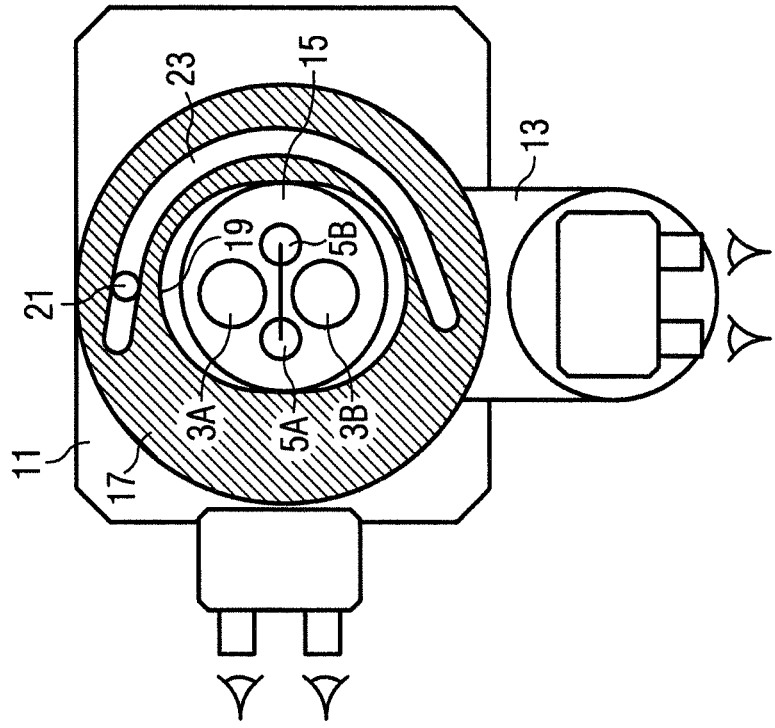

OPERATING MICROSCOPE AND METHOD FOR PIVOTING A CO-OBSERVER MICROSCOPE

BACKGROUND OF THE INVENTION

1. Field of the Invention

The present invention relates to an operating microscope with a main objective that extends along an objective plane and is penetrated by a binocular main observer beam path and a binocular co-observer beam path. Additionally, the invention relates to a method for pivoting a co-observer microscope around a main observer microscope.

2. Description of the Related Art

During surgery carried out with the aid of an operating microscope, it is often desirable, or even necessary, for an assistant of the treating surgeon to likewise be able to observe the operation site in an enlarged fashion through the operating microscope. It is for this reason that operating microscopes are often equipped with a binocular tube for an assistant, the so-called assistant tube or co-observer tube, also referred to as co-observer microscope, in addition to a binocular tube for the main observer, the so-called main observer tube or main observer microscope. Here each tube has its own stereoscopic beam path, wherein the stereoscopic beam paths both penetrate a common main objective. Operating microscopes for main and co-observer are for example distributed by the applicant under the name of OPMI and under the name of OPMI Lumera.

Decoupling the stereoscopic beam path for the co-observers can for example be brought about via physical beam splitters (e.g. partly reflecting mirror surfaces or prism surfaces without total reflection), which decouple part of the observation light intensity from the beam path of the main observer and couple it into the co-observer beam path. Operating microscopes in which physical beam splitters are used for decoupling the co-observer beam path are described in, for example, US 2006/0023300 A1, in DE 102 43 852 B4, DE 197 18 102 A1, DE 33 33 471 A1 and in DE 1 217 099. However, the use of a beam splitter for decoupling the co-observer beam path is afflicted by the disadvantage of neither the main observer nor the co-observer having the full intensity of the observer beam path, and hence the full image brightness, available to them. While this only plays a minor role in operations in which work can be undertaken with intensive illumination, the light loss for the main observer and co-observer cannot always be accepted in eye operations in particular. By way of example, in cataract operations, in which the lens of the eye is removed, a so-called red reflex is used to illuminate the lens during the operation. The red reflex is generated as a result of reddish to orange reflection of the illumination light on the retina. This type of lens illumination is of low intensity because, on the one hand, not all of the illumination light is reflected on the retina and, on the other hand, the illumination intensity on the retina may not be too high so as not to damage the latter. Light loss by beam splitting is therefore generally undesirable in ophthalmological operating microscopes.

In operating microscopes in which there should be no loss of brightness for the main observer and the co-observer, the decoupling of the co-observer beam path is brought about by mirroring surfaces (also referred to as geometric beam splitters) rather than by physical beam splitters, which mirroring surfaces can for example be designed as classical mirrors or as total-reflection prism surfaces. Here, the mirror surfaces for decoupling the co-observer beam path are arranged such that they do not protrude into the partial beam paths of the main observer. Such protrusion would lead to so-called vignetting, that is to say a decrease in light in the main observer beam path. Therefore, vignetting should be avoided where possible. Operating microscopes with mirrors instead of with physical beam splitters for decoupling the co-observer beam path are described in, for example, US 2008/0239473 A1, in DE 10 2004 049 368 A1 and in EP 1 089 107 A1.

Furthermore, it is desirable, or even necessary, for the co-observer also to be able to view the red reflex in ophthalmological operating microscopes. Since the generation of the red reflex presupposes that the angle between the observation beam path and the illumination beam path is as small as possible, the arrangement of the observation pupils in the objective plane of the main objective must be selected such that both the angle between the illumination beam path and the observation beam path of the main observer, and the angle between the illumination beam path and the observation beam path of the co-observer is as small as possible. It is for this reason that use is often made of a pupil arrangement in which the two pupils of the stereoscopic co-observer beam path are arranged, twisted by 90°, between the two pupils of the stereoscopic main observer beam path. By way of example, such arrangements are described in EP 1 089 107 A1 and in U.S. Pat. No. 5,898,518. Here, the co-observer tube can typically be offset by 180°, in order to be able suitably to select the position of the co-observer for an operation on the right or left eye. Such displaceability can be obtained by a rotation of the co-observer tube, as described in EP 1 089 107 A1 and in U.S. Pat. No. 5,898,518. Alternatively, it is also possible for provision to be made for openings in the main microscope for inserting the co-observer tube therein on two opposing sides of the main microscope, as mentioned in, for example, U.S. Pat. No. 5,898,518.

However, in general it is desirable to be able to provide the orientation of the co-observer tube relative to the main observer tube not only in two fixed positions, but to be able to set the orientation in a selective fashion over a range. However, care has to be taken therein for vignetting to be avoided as far as possible in order to prevent noticeable light loss from being brought about for the main observer. At the same time, the co-observer should also, where possible, be provided with the option of being able to view red reflex.

Therefore, it is an object of the present invention to provide an operating microscope that satisfies the aforementioned requirements. It is a further object of the present invention to provide a method for pivoting a co-observer tube in an operating microscope, by means of which the aforementioned requirements can be satisfied.

SUMMARY OF THE INVENTION

An operating microscope according to the invention comprises a main objective with an optical axis and an objective plane that is perpendicular to the optical axis. A binocular main observer beam path has a pair of main observation pupils in the objective plane, the centers of which pupils are interconnected by a first imagined straight line in the objective plane. The operating microscope also has a co-observe microscope that defines a binocular co-observer beam path with a pair of co-observation pupils in the objective plane, the centers of which pupils are interconnected by a second imagined straight line in the objective plane. The first imagined straight line and the second imagined straight line intersect at an angle. Moreover, the operating microscope comprises a displacement arrangement, which allows a displacement of the co-observer beam path with respect to the main observer beam path such that the angle between the first imagined straight line and the second imagined straight line changes during the displacement. This displacement arrangement additionally brings about a displacement of the center point between the co-observation pupils in the objective plane when there is a change in the angle between the first imagined straight line and the second imagined straight line.

There is only very little play for twisting the connecting line between the co-observation pupils with respect to the connecting line of the main observer pupils. This play is determined by the distance of the pupils of a pupil pair from one another and by the diameter of the pupils of a pupil pair. As explained at the outset, the red reflex should be observable, where possible, for the main observer and the co-observer. Thus, the pupils are selected to be as large as possible in order to allow image brightness that is as high as possible. On the other hand, there are limits to the distance between the pupils of a pupil pair by the size of the objective lens, and so operating microscopes according to the prior art are generally designed such that an arrangement of the two pupil pairs with an angle of 90° with respect to one another does not lead to vignetting of the main observer beam path. The invention is now based on the realization that such vignetting can be avoided if the center point between the co-observer pupils in the plane of the main objective is displaced at the same time that the angle of intersection between the first and the second imagined lines is changed. This displacement allows better utilization of the space between the two pupils of the main observer beam path. At the same time, the angle between the illumination beam path and the co-observer beam path can be kept small, and so observation of the red reflex also remains possible for the co-observer.

The first imagined straight line and the second imagined straight line will typically intersect at an angle of 90° in a first position of the co-observer beam path. The displacement arrangement then allows twisting of the second imagined straight line, that is to say the connecting line between the center points of the co-observer pupils, with respect to the first imagined straight line, that is to say the connecting line between the main observation pupils, by an angle of at least 5°, more particularly of at least 10° and preferably of at least 15°. Preferably this allows both clockwise twisting of the second imagined straight line with respect to the first imagined straight line and counterclockwise twisting of the second imagined straight line with respect to the first imagined straight line. The aforementioned play when twisting the co-observer beam path allows optimization of the positioning of the co-observer in relation to the main observer by pivoting the co-observer tube, in which it goes without saying that larger play for twisting significantly increases the positioning options.

The displacement of the center point between the centers of the co-observation pupils in the objective plane is advantageously brought about along a prescribed path. Said path can more particularly lead around one of the two main observation pupils. It can moreover be designed in particular as an elliptical path, which leads around a pupil of the main observer beam path for the aforementioned guiding.

In order to implement the displacement along a prescribed path, the displacement arrangement can have a forced guide, which brings about a displacement of the center point between the co-observation pupils in the objective plane along the prescribed path when the second imagined straight line is twisted with respect to the first imagined straight line. Such a refinement of the operating microscope can be implemented by purely mechanical means, and so a defined displacement of the center point can also be brought about when the co-observer tube is pivoted by hand.

In a constructive refinement of the forced guide, the operating microscope has a main microscope with an optical axis and a stereoscopic main observation beam path, and with a co-observer microscope that can be pivoted around the optical axis and has a stereoscopic co-observer beam path. The co-observer beam path is guided out of the main microscope by means of at least one light-deflecting element of the co-observer microscope, which can in particular be designed as a mirror, but also as a prism that has been suitably selected. The main microscope or the co-observer microscope has a projection, for example a pin or cam, which interacts with a guide element, for example a slot or guide surface. If the projection is on the main microscope, the guide element is arranged on the co-observer microscope; if the projection is arranged on the co-observer microscope, the guide element is located on the main microscope. The guide element is designed such that it impresses, for example by means of a pin engaging in a guide groove or a cam pressed against a guide surface, a translational movement onto the co-observer microscope during pivoting.

As an alternative to a purely mechanically guided displacement of the center point between the co-observation pupils when pivoting the co-observer beam path with respect to the main observer beam path, it is also possible for the displacement of the center point to be implemented by electronic means. In this case, the displacement arrangement of the operating microscope has a drive, for example an electrical drive, which allows electronically controlled displacement of the co-observer beam path in a plane parallel to the object plane. Then there also is a control unit that determines a displaced position of the center point between the co-observation pupils for each angle that can be set between the second imagined straight line and the first imagined straight line. In particular, the displaced position of the center point can in this case be determined on the basis of a formulaic relationship for the position of the center point as a function of the angle, or on the basis of a spreadsheet in which the respective displaced position is specified for a number of angles.

In a further alternative refinement which can be used for implementing the displacement of the center point, the operating microscope comprises a main microscope with an optical axis, a housing and at least one insert opening available in the housing for inserting a co-observer microscope. The insert opening has a larger dimension in a circumferential direction of the housing in respect of the optical axis than the co-observer microscope to be inserted, and so the co-observer microscope can be inserted into the insert opening in different pivot positions in respect of the optical axis. Furthermore, there are spacers that fix the co-observer microscope in a fixed pivot position in the insert opening and fix the distance between the co-observer microscope and the optical axis as a function of the pivot position.

In particular, the spacers can be implemented as adaptor inserts, the external dimensions of which are matched to the internal dimensions of the insert opening in the housing of the main microscope such that they can be inserted without play into the insert opening. Moreover, the adaptor inserts have an adaptor opening matched to the external dimensions of the co-observer microscope such that the co-observer microscope can be inserted without play into the adaptor opening. In the adaptor opening there is a stop, which fixes how far the co-observer microscope can be inserted into the adaptor opening. In this refinement at least two adaptor inserts are available, which differ from one another in the position of their adaptor opening and the depth of their stops in the adaptor opening. Thus, a suitably selected adaptor opening can be used to fix the location of the co-observation pupils in the objective plane of the main objective, and so the invention can also be implemented in combination with co-observer microscopes that can be plugged in.

In a further advantageous refinement of the operating microscope according to the invention, said operating microscope has an illumination arrangement for 0°-illumination or coaxial illumination of an observation object. In the case of the 0°-illumination, the illumination arrangement is designed such that the illumination beam path is guided onto the observation object parallel to the optical axis of the main objective through the center point between the main observation pupils. By contrast, in the case of coaxial illumination, the illumination is brought about by means of two partial illumination beam paths that are directed to the observation object coaxial to the partial observation beam paths of the main observer beam path. In the case of both the 0°-illumination and the coaxial illumination, it is possible for the illumination directions to deviate slightly from the strict 0°-illumination or the strict coaxial illumination, without this preventing the observation of red reflex. More particularly, deviations of up to at most 6°, preferably up to at most 2°, should also within the scope of the invention be considered 0°-illumination or coaxial illumination.

The invention also relates to a method for pivoting a co-observer microscope of an operating microscope with a main microscope. The main microscope has a stereoscopic main observer beam path, the co-observer microscope has a stereoscopic co-observer beam path. The main microscope has a main objective with an optical axis, an objective plane that is perpendicular to the optical axis. The objective plane is intersected by both the binocular main observer beam path and a binocular co-observer beam path. The binocular main observer beam path has a pair of main observation pupils in the objective plane, the centers of which pupils are interconnected by a first imagined straight line running in the objective plane. Similarly, the binocular co-observer beam path has a pair of co-observation pupils in the objective plane, the centers of which pupils are interconnected by a second imagined straight line in the objective plane. The first imagined straight line and the second imagined straight line intersect at an angle. The method of the invention includes displacing the center point between the co-observation pupils in the objective plane when pivoting the co-observer microscope around the optical axis of the main objective. Here, the displacement of the center point between the co-observation pupils can be brought about in the objective plane along a prescribed path. More particularly, this path can guide the center point between the co-observer pupils around one of the two main observer pupils, for example on a prescribed elliptical path.

The method according to the invention can implement the properties and advantages already described with respect to the operating microscope according to the invention.

Further features, properties and advantages of the present invention emerge from the following description of exemplary embodiments with reference to the attached figures.

BRIEF DESCRIPTION OF THE DRAWINGS

FIG. 4 shows a schematic illustration of a first exemplary embodiment of an operating microscope according to the invention, wherein the co-observation pupils are arranged at an angle of 90° with respect to the main observation pupils.

FIG. 5 shows the operating microscope from FIG. 4, wherein the co-observation pupils are arranged at an angle not equal to 90° with respect to the main observation pupils.

DETAILED DESCRIPTION OF THE PREFERRED EMBODIMENTS

Figure 1:
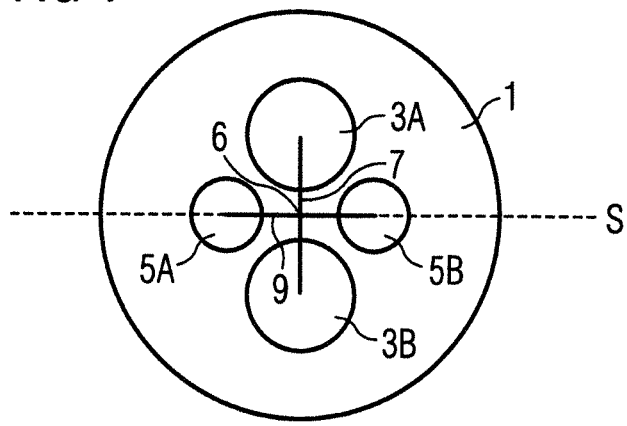
FIG. 1 shows the main observation pupils and the co-observation pupils of an operating microscope in a section through the objective plane of the main objective, wherein the pupils are arranged at an angle of 90° to one another.
Figure 2:
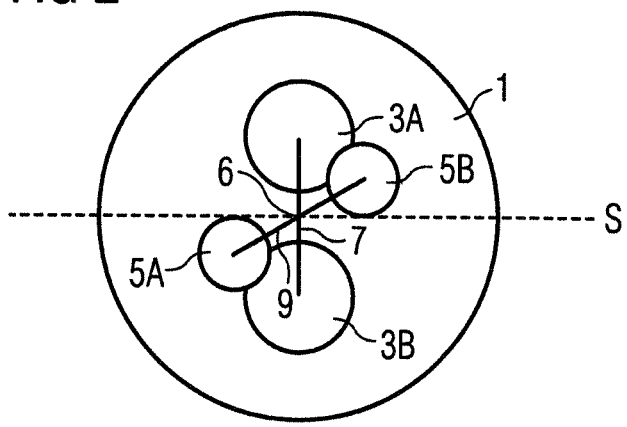
FIG. 2 shows the section from FIG. 1 in the case of arranging the observation pupils at an angle not equal to 90° without implementing the invention.
Figure 3:
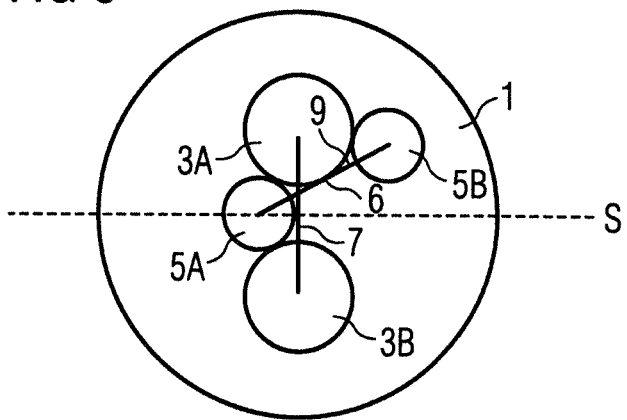
FIG. 3 shows the section from FIG. 2 with an arrangement of the co-observation pupils at the angle from FIG. 2 when implementing the invention.

Hereinbelow, FIGS. 1 to 3 are first of all used to explain the underlying principle of the invention before exemplary embodiments of operating microscopes, in which the principle according to the invention has been implemented, are subsequently described.

FIG. 1 shows a section along the objective plane of the main objective 1 of an operating microscope with a main observer microscope and a co-observer microscope, and also shows the observation pupils 3a, 3b of the stereoscopic main observer beam path and the co-observation pupils 5a, 5b of the stereoscopic co-observer beam path. Moreover, imagined connecting lines 7, 9 are indicated, which interconnect the centers of the two main observation pupils 3a, 3b or the two co-observation pupils 5a, 5b.

The main observation beam path with the main observation pupils 3a, 3b passes through a main observer microscope (not illustrated in FIGS. 1-3), whereas the co-observation beam path with the co-observation pupils 5a, 5b passes through a co-observer microscope (likewise not illustrated in FIGS. 1-3). Here the main objective 1 is common to both beam paths, that is to say it is penetrated by both the main observer beam path and the co-observer beam path. The co-observation beam path is coupled out of the main observer microscope and into the co-observer microscope by means of a common mirror for both partial beam paths or by means of two separate mirrors. In order to avoid covering the main observation pupils 3a, 3b by the mirror or mirrors, the mirror (s) is/are selected to be just so large in terms of their size such that they are able to decouple the two stereoscopic partial beam paths of the co-observer beam path. Their size therefore largely corresponds to the size of the co-observation pupils 5a, 5b.

A common configuration of main observer microscope and co-observer microscope is such that the imagined connecting line 9 between the centers of the co-observation pupils 5a, 5b intersects the imagined connecting line 7 between the centers of the main observation pupils 3a, 3b at an angle of 90°, as illustrated in FIG. 1. The co-observer is then in a position offset by an angle of 90° with respect to the main observer, wherein it can in principle be located to the left or the right of the main observer. By way of example, the side on which the co-observer is located can within the scope of eye operations depend on which eye is intended to be operated on. As mentioned at the outset, operating microscopes therefore often have the option of pivoting the co-observer microscope by 180°, or uninstalling the latter from a first installation position and reinstalling it in a position pivoted by 180°.

However, in general it is desirable that the co-observer microscope can be used not only in these two installation positions or pivot positions. By way of example, it can be desirable for the angle at which the co-observer is positioned relative to the main observer to be greater than 90°, for example to offer the observers more space for surgical acts. However, a difficulty associated with this is that pivoting the co-observer microscope in order to enlarge the angle between the imagined line 9 connecting the centers of the co-observation pupils 5a, 5b and the imagined line 7 connecting the centers 3a, 3b of the main observer pupils would result in the co-observation pupils 5a, 5b partly covering the main observation pupils 3a, 3b, as illustrated in FIG. 2. This in turn would lead to the decoupling mirror or mirrors for the co-observation beam path protruding into the main observation beam path and would thus bring about vignetting of the main observer beam path. Since the brightness of the observation image is low, particularly in eye operations with red reflex illumination, a further loss of brightness due to vignetting is not desirable.

In order to avoid vignetting of the main observer beam path when the co-observer microscope is pivoted around the optical axis of the main observer microscope, the center point 6 between the co-observation pupils 5a, 5b is therefore, according to the invention, at the same time displaced in the objective plane during pivoting. By way of example, this affords the possibility of bringing about the arrangement of the co-observation pupils 5a, 5b relative to the main observation pupils 3a, 3b illustrated in FIG. 3. Here, the pivot angle illustrated in FIG. 3 corresponds to the pivot angle illustrated in FIG. 2. It can be seen that vignetting of the main observer beam path can at least to a large extent be avoided by virtue of the fact that the center point between the means-observation pupils 5a, 5b has in comparison with the arrangement illustrated in FIG. 2 been displaced by an amount along the connecting line 7 between the centers of the main observation pupils 3a, 3b and by an amount perpendicular to this connecting line. More particularly, this displacement can be made to depend on the pivot angle, for example by having a smaller displacement in the case of smaller pivot angles than the one illustrated in FIG. 3. What this can achieve is that the center point 6 between the co-observation pupils 5a, 5b moves around one of the partial beam paths of the main observer beam path when pivoting the co-observation microscope.

The displacement of the center point between the co-observation pupils 5a, 5b within the objective plane of the main objective 1 can in principle be implemented by mechanical means or, in the case of motor-driven pivot movements, by electronic means.

Reference is still made to the fact that although the displacement of the center point 6 illustrated in FIG. 3 is brought about toward the top and right, it in principle can also be brought about toward the bottom and left. Likewise, a clockwise rotation can in principle also be implemented instead of a counterclockwise rotation. By way of example, in this case this would result in a configuration of the co-observation pupils 5a, 5b that would be obtained by mirroring the illustrated configuration through the mirroring straight-line S indicated by a dashed line.

An operating microscope implementing the principle according to the invention can allow pivoting of the co-observer microscope from the 90° position illustrated in FIG. 1 by up to 25° and more in both clockwise and counterclockwise directions. What pivot angles can be implemented in this case depends on the distance between the main observation pupils 3a, 3b and the diameter of the co-observation pupils 5a, 5b. Larger pivot angles can be implemented in the case of large distances and small diameters than in the case of small distances and large diameters of the co-observation pupils 5a, 5b. Here, reference should be made to the fact that the co-observation pupils 5a, 5b generally have a smaller diameter than the main observation pupils.

A first exemplary embodiment for implementing the described displacement of the center point 6 between the co-observation pupils 5a, 5b when pivoting the co-observer microscope is illustrated in FIGS. 4 and 5. The figures show an operating microscope that comprises a main microscope 11 and a co-observer microscope 13. The co-observer microscope 13 is mounted such that it can pivot around a cylindrical section 15 of the main microscope, wherein the pivot mechanism and the decoupling mirror or mirrors for the co-observer beam path and possibly further optical elements such as prisms for erecting the image are integrated into the housing of the main microscope.

The section 17 of the co-observer microscope 13 arranged around the cylindrical section 15 is provided with a slot guide 19, which is penetrated by the cylindrical section 15 of the main microscope. The slot guide 19 thereby also allows a longitudinal displacement of the co-observer microscope 13 in the longitudinal direction thereof in addition to a pivot movement of the co-observer microscope 13 around the optical axis of the main observer microscope 11.

Linking a pivot movement with a defined longitudinal movement is implemented by a bolt 21, which is arranged on the co-observer microscope 13 and engages in a guide groove 23 found on the main microscope 11. Starting from the position illustrated in FIG. 4, this groove follows a path deviating from a circular form in a pivot range of ±25°, which path causes the decoupling mirror or mirrors to move around a partial beam path of the main microscope when pivoting the co-observer microscope 13 in this angular range—and hence the movement of the co-observation pupils 5a, 5b around one of the main observation pupils 3a, 3b, as described with reference to FIG. 3. More particularly, the guide groove can be designed such that the movement of the center point between the co-observation pupils 5a, 5b follows an elliptical path. A pivoted position of the co-observer microscope 13 is illustrated in FIG. 5.

Since the described refinement implements the displacement of the center point 6 between the co-observation pupils 5a, 5b purely by mechanical means, this refinement is also particularly suitable for operating microscopes in which the pivot movement should be performed manually. However, it can in principle also be used in operating microscopes in which the pivot movement is motor driven.

Although the bolt 21 is arranged on the co-observer microscope 13 and the guide groove 23 is arranged on the main microscope 11 in the exemplary embodiment described with reference to FIGS. 4 and 5, the guide groove 23 can also be arranged on the co-observer microscope 13 and the bolt 21 can be arranged on the main microscope. Moreover, in principle it is also possible for the guide to be implemented in a different fashion, for example by means of a cam that is pressed against a guide surface.

Figure 6:
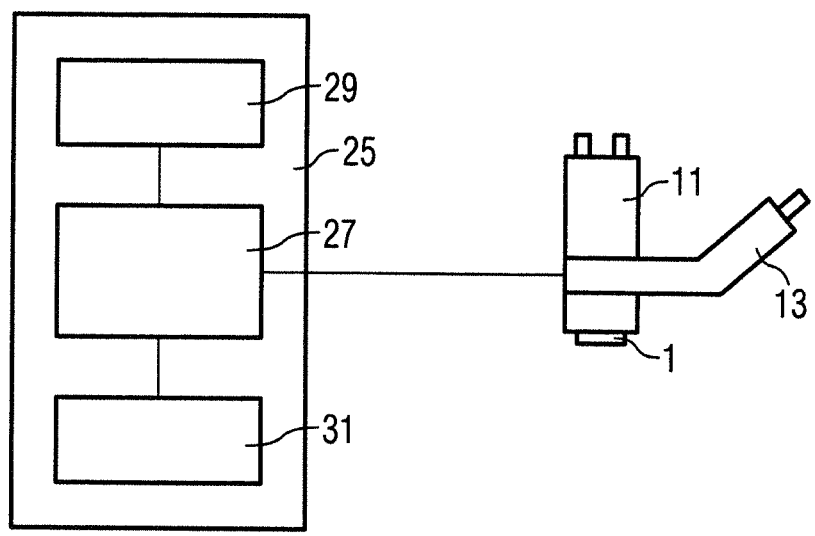
FIG. 6 shows a schematic illustration of a second exemplary embodiment of an operating microscope according to the invention.

FIG. 6 illustrates a second exemplary embodiment of an operating microscope by means of which the displacement of the center point 6 between the co-observation pupils 5a, 5b can be implemented. In addition to an operating microscope with a main observer microscope 11 and a co-observer microscope 13, which can for example be pivoted around the main microscope 11 by being driven by an electromotor, the figure shows a control unit 25, which is illustrated as a block diagram. For the purposes of electronic control, the control unit 25 acts on the drive for pivoting the co-observer microscope 13.

The control unit 25 comprises a central processing unit 27, which is connected, on the one hand, to the drive of the microscope for emitting control signals and, on the other hand, to a storage medium 29 for receiving stored data. Moreover, the central processing unit 27 is connected to an input unit 31, for example a touch screen, by means of which a pivot angle for the co-observer microscope 13 can be selected. The storage medium 29 contains a spreadsheet in which the respective displacement of the center point 6 between the co-observation pupils 5a, 5b in the objective plane to be carried out is stored for a number of pivot angles.

If a user of the operating microscope selects a pivot angle for the co-observer microscope 13 with the aid of the input arrangement 31, the central processing unit 27 accesses the spreadsheet located in the storage medium 29 in order to recall the associated displacement of the co-observer microscope 13 parallel to the objective plane. The central processing unit 27 then generates control data for the drive on the basis of the data representing the displacement to be set, which drive then displaces the co-observer microscope 13 into the appropriate position.

Rather than being in the form of a spreadsheet, the assignment of suitable displacements of the center point 6 between the co-observation pupils 5a, 5b in the objective plane to the respective pivot angles can also be stored in the form of a functional relationship. In this case, the central processing unit calculates an associated displacement of the center point 6 on the basis of the functional relationship when the pivot angle to be set is received.

Figure 7:
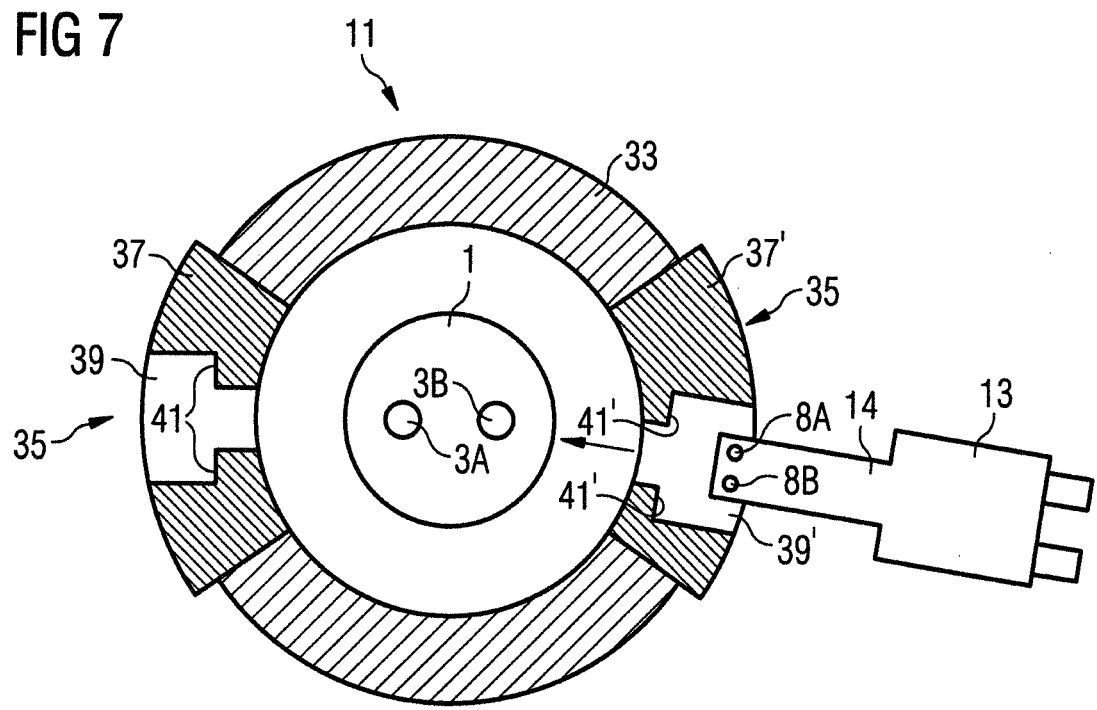
FIG. 7 shows a schematic illustration of a third exemplary embodiment of an operating microscope according to the invention.

FIG. 7 illustrates a third exemplary embodiment for an operating microscope in which the displacement of the center point 6 between the co-observation pupils 5a, 5b is implemented when the pivot position of the co-observer microscope 13 is changed. This figure shows an operating microscope in a very schematic illustration, in which the co-observer microscope 13 is not fixedly arranged, but can be inserted through openings 35 in the housing 33 of the main microscope 11. The figure shows the housing 33, which basically is of a cylindrical shape in the present exemplary embodiment, of the main microscope 33, and a co-observer microscope 13.

The housing 33 of the main microscope 11 has two mutually opposing openings 35, which extend over a predefined angular region in the circumferential direction of the housing 33 in respect of the optical axis of the main microscope 11. This angular range is greater than what would be necessary for the insertion of the co-observer microscope 13. This affords the possibility of inserting the co-observer microscope 13 in various pivot positions into an opening in the housing 33 of the main observer microscope 11.

Adaptor inserts 37, the external dimensions of which are matched to the internal dimensions of the openings 35 in the housing 33 of the main microscope 11 such that it can be inserted without play into the openings 35, are used for fixing the pivot position, and hence the angle between the imagined line 9 connecting the centers of the co-observation pupils 5a, 5b and the imagined line 7 connecting the centers of the main observation pupils 3a, 3b. In the present exemplary embodiment, the adaptor inserts 37 substantially have the shape of a cylinder-shell section. They are provided with adaptor openings 39, which substantially extend through the adaptor inserts 37 in the radial direction and the dimensions of which are matched to the dimensions of the part of the co-observer microscope 13 to be inserted into the main microscope 11 such that the co-observer microscope 13 can be inserted without play into the openings. The position of the adaptor openings 39 in various adaptor inserts 37, 37' in the circumferential direction of the cylinder-shell section can differ, and so the respective position determines the pivot position of an inserted co-observer microscope 13. The adaptor openings 39 are moreover provided with stops 41, 41', which fix how deep the co-observer microscope 13 can be inserted into the adaptor opening 39.

It can be seen in FIG. 7 that there are at least two different adaptor inserts 37, 37' in the operating microscope according to the invention, which differ from one another in both the position of their adaptor openings 39, 39' and the depth position of their stops 41, 41' in the adaptor opening 39. This affords the possibility of adapting the position of the decoupling mirrors 8a, 8b in respect of their position parallel to the plane of the main objective 1 in a co-observer microscope 13 inserted into the main microscope 11 to the pivot position which the co-observer microscope 13 assumes in respect of the optical axis of the main microscope 11 after being inserted into the adaptor opening 39, 39'.

Although merely two different adaptor inserts 37, 37' were described with reference to FIG. 7, there can also be an increased number of adaptor inserts if it should be possible to implement a larger number of pivot positions.

The opening 35 in the housing 33 of the main microscope 11 respectively not utilized by the co-observer microscope 13 can be closed by a bladed shutter in order to avoid stray light and contamination.

The described operating microscopes can more particularly be designed as ophthalmological operating microscopes, which comprise an illumination arrangement, which allow either a zero-degree illumination or a coaxial illumination of the operating field. In the case of a zero-degree illumination, the illumination would be brought about parallel to the optical axis of the main objective 1 or at a small angle of at most 2 to 6° from the optical axis of the main objective. By contrast, in the case of coaxial illumination, the illumination would be brought about over two partial illumination beam paths, which run coaxially (or at a small angle of at most 2 to 6°) to the partial observation beam paths of the main observer. Such illumination is necessary in particular when red reflex in the eye should be observable. In such operating microscopes, the arrangement of the observation pupils illustrated in FIG. 1 is such that the imagined connecting lines 7, 9 between the observation pupils 3a, 3b of the main observation beam path and the observation pupils 5a, 5b of the co-observation beam path intersect is advantageous because then coaxial or zero-degree illumination can be implemented at the same time for both the main observer beam path and the co-observer beam path, which allows an observation of the red reflex. By way of example, in the case of coaxial illumination along the main observer beam path, the former constitutes zero-degree illumination for the co-observation beam path, wherein, as mentioned above, a deviation of up to 2 to 6° from the optical axis should still be considered zero-degree illumination for the main observer. In the case of zero-degree illumination in respect of the main observer, that is to say illumination extending along the optical axis of the main objective 1, this constitutes zero-degree illumination for both the main observer and the co-observer. These relationships do not change significantly by the displacement of the center point 6 according to the invention between the observation pupils 5a, 5b of the co-observation beam path. Therefore, in conclusion, the observation of red reflex can be afforded for both the main observer and the co-observer even in the case of pivoting according to the invention with simultaneous displacement of the center point between the co-observation pupils.

The exemplary embodiments were used to describe operating microscopes which allow the implementation of the principle according to the invention of displacing the center point between the co-observation pupils in a plane parallel to the objective plane when changing the pivot position of the co-observer microscope.

What is claimed is:

1. An operating microscope comprising:
a binocular main microscope (11) with a main objective (1) having an optical axis, an objective plane that is perpendicular to the optical axis and a binocular main observer beam path intersecting the main objective at two main observation pupils (3a, 3b) in the objective plane, the main observation pupils having centers interconnected by a first straight line (7) in the objective plane,
a binocular co-observer microscope (13) with a binocular co-observer beam path intersecting the main objective at two co-observation pupils (5a, 5b) in the objective plane, the co-observation pupils having centers interconnected by a second straight line (9) in the objective plane, the second straight line (9) having a center (6) point between the co-observation pupils,
the first straight line (7) and the second straight line (9) intersecting at an angle, and
a displacement arrangement that allows a displacement of at least a part of the co-observation microscope (13) so that the co-observer beam path displaces with respect to the main observer beam path such that the angle between the second straight line (9) and the first straight line (7) changes during the displacement, and so that the center point (6) between the co-observation pupils (5a, 5b) in the objective plane displaces when there is a change in the angle between the second straight line (9) and the first straight line (7).

2. The operating microscope of claim 1, wherein the second imagined straight line (9) and the first straight line (7) intersect at an angle of 90° in a first position of the co-observer beam path and the displacement arrangement allows a twisting of the second straight line (9) with respect to the first imagined straight line (7) by an angle of at least 5°.

3. The operating microscope of claim 2, wherein the displacement arrangement is configured to allow displacement of at least a part of the co-observation microscope to achieve both clockwise twisting of the second imagined straight line (9) with respect to the first imagined straight line (7) and counterclockwise twisting of the second imagined straight line (9) with respect to the first imagined straight line (7).

4. The operating microscope of claim 1, wherein the displacement of the center point (6) between the centers of the co-observation pupils (5a, 5b) in the objective plane is brought about along a prescribed path.

5. The operating microscope of claim 4, wherein the prescribed path guides the center point (6) between the co-observer pupils (5a, 5b) around one of the two main observer pupils (3a, 3b).

6. The operating microscope of claim 5, wherein the prescribed path is an elliptical path.

7. The operating microscope of claim 4, wherein the displacement arrangement has a forced guide (21, 23) and a slot guide (15, 19), which brings about a displacement of the center point (6) between the co-observation pupils (5a, 5b) in the objective plane along the prescribed path when the second imagined straight line (9) is twisted with respect to the first imagined straight line (7).

8. The operating microscope of claim 7, wherein the binocular main observation beam path of the main microscope (11) is and a stereoscopic main observer beam path, and the co-observer microscope (13) is disposed to be pivoted around the optical axis of the main microscope (11) and the binocular co-observer beam path is a stereoscopic co-observer beam path, wherein
the co-observer beam path is guided out of the main microscope (11) by at least one light-deflecting element (8a, 8b) of the co-observer microscope (13), and
the main microscope (11) or the co-observer microscope (13) has a projection (21) that interacts with a guide element (23) of the respective other microscope, wherein the guide element (23) is designed such that it impresses a translational movement onto the co-observer microscope (13) during pivoting.

9. The operating microscope of claim 1, wherein the displacement arrangement has a drive that allows electronically controlled displacement of the co-observer beam path in a plane parallel to the objective plane, and the operating microscope further comprising a control unit (25) that determines a displaced position of the center point (6) between the co-observation pupils (5a, 5b) for each angle that can be set between the second imagined straight line (9) and the first imagined straight line (7).

10. The operating microscope of claim 1, wherein the main microscope (11) has a housing (33) and at least one insert opening (35) in the housing (33) for inserting the co-observer microscope (13), the insert opening having a larger internal dimension in a circumferential direction of the housing (33) in respect of the optical axis than external dimensions of the co-observer microscope (13) to be inserted, and so the co-observer microscope (13) can be inserted into the insert opening in different pivot positions in respect of the optical axis, further comprising spacers that fix the co-observer microscope (13) in a fixed pivot position in the insert opening (35) and fix the distance between the co-observer microscope (13) and the optical axis as a function of the pivot position.

11. The operating microscope of claim 10, wherein the spacers are adaptor inserts (37), the external dimensions of which are matched to the internal dimensions of the insert opening (35) in the housing of the main microscope (11) such that the adapter inserts can be inserted without play into the insert opening, the adaptor inserts having an adaptor opening (39) matched to the external dimensions of the co-observer microscope (13) such that the co-observer microscope (13) can be inserted without play into the adaptor opening, and the adaptor inserts being equipped with a stop (41) that fixes how far the co-observer microscope (13) can be inserted into the adaptor opening (39), the adapter inserts comprising at least two adaptor inserts (37) that differ from one another in the position of their adaptor opening (39) and the depth of their stops (41) in the respective adaptor opening (39).

12. The operating microscope of claim 1, further comprising an illumination arrangement for 0°-illumination or coaxial illumination of an observation object.

13. A method for adjusting an operating microscope that has a main microscope (11) with a main objective (1) that has an optical axis, an objective plane that is perpendicular to the optical axis and a stereoscopic main observer beam path intersecting the main objective at two main observation pupils (3a, 3b) in the objective plane, the main observation pupils having centers interconnected by a first straight line (7) in the objective plane, and a co-observer microscope (13) having a stereoscopic co-observer beam path intersecting the main objective at two co-observation pupils (5a, 5b) in the objective plane, the co-observation pupils (5a, 5b) having centers interconnected by a second straight line (9) in the objective plane, the first imagined straight line (7) and the second straight line (9) intersect at an angle, the method comprising: displacing the center point (6) between the co-observation pupils (5*a*, 5*b*) the objective plane when pivoting the co-observer microscope (13) around the optical axis of the main objective (1).

14. The method of claim 13, wherein displacement of the center point (6) between the co-observation pupils (5*a*, 5*b*) in the objective plane is brought about along a prescribed path.

15. The method of claim 14, wherein the prescribed path guides the center point (6) between the co-observer pupils (5*a*, 5*b*) around one of the two main observer pupils (3*a*, 3*b*).

16. The method of claim 15, wherein the prescribed path is an elliptical path.

17. An adaptor insert (37) for the operating microscope of claim 12, wherein external dimensions of the adaptor insert (37) are matched to internal dimensions of an insert opening (35) in the housing of the main microscope (11) such that the adaptor insert (37) can be inserted without play into the insert opening, and the adaptor insert (37) has an adaptor opening (39) matched to the external dimensions of the co-observer microscope (13) such that the co-observer microscope (13) can be inserted without play into the adaptor opening (39), and the adaptor opening (39) is equipped with a stop (41) that fixes how far the co-observer microscope (13) can be inserted into the adaptor opening (39).

* * * * *